United States Patent [19]
Weston

[11] Patent Number: 5,891,086
[45] Date of Patent: *Apr. 6, 1999

[54] NEEDLE-LESS INJECTOR

[75] Inventor: Terence Edward Weston, Suffolk, United Kingdom

[73] Assignee: Weston Medical Limited, Suffolk, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 591,585

[22] PCT Filed: Jul. 27, 1994

[86] PCT No.: PCT/GB94/01608

§ 371 Date: Jan. 16, 1996

§ 102(e) Date: Jan. 16, 1996

[87] PCT Pub. No.: WO95/03844

PCT Pub. Date: Feb. 9, 1995

[30] Foreign Application Priority Data

Jul. 31, 1993 [GB] United Kingdom .................... 9315915
Sep. 28, 1993 [GB] United Kingdom .................... 9319981

[51] Int. Cl.$^6$ ................................................ A61M 5/30
[52] U.S. Cl. ................................ 604/70; 604/68; 604/145
[58] Field of Search ................................ 604/68, 69, 70, 604/131, 132, 134, 135, 140, 141, 143, 49, 51; 124/63, 65, 71

[56] References Cited

U.S. PATENT DOCUMENTS

| | | |
|---|---|---|
| 2,322,244 | 6/1943 | Lockhart . |
| 2,322,245 | 6/1943 | Lockhart . |
| 2,380,534 | 7/1945 | Lockhart . |
| 2,398,544 | 4/1946 | Lockhart . |
| 2,550,053 | 4/1951 | Garwood et al. . |

(List continued on next page.)

FOREIGN PATENT DOCUMENTS

| | | |
|---|---|---|
| 0 276 158 | 7/1988 | European Pat. Off. . |
| 0 347 190 | 12/1989 | European Pat. Off. . |
| 0 409 674 | 1/1991 | European Pat. Off. . |
| 499 481 A1 | 2/1992 | European Pat. Off. . |
| 2 629 348 | 10/1989 | France . |
| 2 254 153 | 5/1974 | Germany . |
| 88 13 938 | 12/1989 | Germany . |
| 41 29 271 | 9/1992 | Germany . |
| 195060 | 4/1967 | Russian Federation . |
| 705515 | 3/1954 | United Kingdom . |
| 971162 | 9/1964 | United Kingdom . |
| 993309 | 5/1965 | United Kingdom . |
| WO 82/02735 | 9/1982 | WIPO . |
| WO 90/0196 | 3/1990 | WIPO . |
| 92 08508 | 5/1992 | WIPO . |
| WO 93/03779 | 3/1993 | WIPO . |

Primary Examiner—Ronald Stright, Jr.
Assistant Examiner—At Nguyen
Attorney, Agent, or Firm—Darby & Darby

[57] ABSTRACT

In a needle-less injector combining an actuator and a medicament cartridge, the actuator includes a housing with a forward portion to which the cartridge is connected. An impact member is mounted within the housing inward of the forward portion so as to be movable toward the forward portion, where it may strike components of the cartridge to effect expulsion of a dose of medicament. A chamber is provided within the housing and is pre-filled with a pressurized gas which is in communication with and exerts a constant force on the impact member, tending to urge it towards the forward portion. Movement of the impact member is prevented by a latch which normally engages the impact member and prevents its forward movement, but is actuable to be moved out of such engagement, permitting movement of the impact member, the cartridge includes a piston which is mounted in the body of the cartridge with an interference fit and is made of a material which is substantially non-resilient when subjected to a slowly applied force, but is highly resilient when subjected to a rapidly applied force.

25 Claims, 7 Drawing Sheets

U.S. PATENT DOCUMENTS

| | | |
|---|---|---|
| 2,689,566 | 9/1954 | Lockhart . |
| 2,693,184 | 11/1954 | Lockhart . |
| 2,693,185 | 11/1954 | Lockhart . |
| 2,695,614 | 11/1954 | Lockhart . |
| 2,724,383 | 11/1955 | Lockhart . |
| 2,737,946 | 3/1956 | Hein, Jr. . |
| 2,764,977 | 10/1956 | Ferguson et al. . |
| 2,772,369 | 9/1956 | Venditty . |
| 3,115,133 | 12/1963 | Morando . |
| 3,650,084 | 3/1972 | Moreland . |
| 3,688,765 | 9/1972 | Gasaway ............................ 604/143 X |
| 3,782,380 | 1/1974 | Van Der Gaast . |
| 3,797,489 | 3/1974 | Starnoff . |
| 3,802,430 | 4/1974 | Schwebel . |
| 3,859,996 | 1/1975 | Mizzy . |
| 4,059,107 | 11/1977 | Iriguchi et al. . |
| 4,089,334 | 5/1978 | Schwebel et al. . |
| 4,403,609 | 9/1983 | Cohen . |
| 4,421,508 | 12/1983 | Cohen . |
| 4,507,113 | 3/1985 | Dunlap . |
| 4,518,385 | 5/1985 | Lindmayer et al. . |
| 4,561,856 | 12/1985 | Cochran . |
| 4,596,556 | 6/1986 | Morrow et al. . |
| 4,709,686 | 12/1987 | Taylor et al. . |
| 4,744,786 | 5/1988 | Hooven . |
| 4,771,758 | 9/1988 | Taylor et al. . |
| 4,913,699 | 4/1990 | Parsons . |
| 5,062,830 | 11/1991 | Dunlap . |
| 5,193,517 | 3/1993 | Taylor et al. . |
| 5,279,576 | 1/1994 | Loo et al. . |
| 5,281,202 | 1/1994 | Weber et al. . |
| 5,334,144 | 8/1994 | Alchas et al. ............................ 604/68 |
| 5,599,302 | 2/1997 | Lilley et al. . |

NEEDLE-LESS INJECTOR

BACKGROUND OF THE INVENTION

1. Field of the Invention

The present invention relates to a needle-less injector, wherein a dose of liquid medicament is discharged in a thin jet at sufficient velocity to penetrate the epidermis of the human, plant or animal to be treated, thus to introduce the medicament into the tissues of the subject.

2. Description of the Prior Art

Needle-less injectors are uses as an alternative to hypodermic needle type injectors for delivery drugs, vaccines, local anaesthetics and other fluids into the tissues. The medicament is discharged in a jet at high velocity to first puncture the epidermis, and thereafter be deposited in the tissues of the subject. A variation is to press the discharge nozzle onto the epidermis and force the medicament at very high pressure through the epidermis.

Such injectors offer many potential benefits: because the hole made by the jet is smaller than that made by a needle, less pain is experienced by the patient when compared with hypodermic needle injection; the availability of the medicament to the capillaries is often enhanced because the spread of the medicament within the tissues is much greater than achieved with a needle injection, which deposits the medicament as a bolus at the needle tip; there is less chance of cross-contamination; animals, which are frequently uncooperative, are more easily injected, because there is no risk of a needle breaking or bending, and the injection is accomplished much faster than needle injection; there is no needle disposal problem; the risk of so-called needle-stick injury is eliminated.

Prior art devices typically use a spring-loaded piston pump to generate the injection pressure, in which the piston is retracted against a spring to withdraw fluid from a reservoir. At the end of the piston stroke (which may be adjustable) the piston is disengaged from the retracting mechanism and is urged suddenly by the spring to pressurise and discharge the fluid from the delivery nozzle. The retracting mechanism may be manual or motorised. In some devices, the piston is driven on the discharge stroke by gas or an electric motor instead of a spring.

Manually operated injectors generate a pressure in the medicament of about 100 bars. In operation, the discharge orifice is placed a small distance (about 10 mm) from the epidermis, and the high velocity jet strikes then penetrates the epidermis (free jet mode). The principle appears to be that the jet sacrifices some of its kinetic energy to puncture the epidermis, because if the nozzle is pressed firmly on the skin (contact mode), and the injector operated, the liquid is pressurised but has no kinetic energy, and is unable to pierce the skin. In the jet free mode, medicament is wasted, since some of the liquid is deflected sideways before puncture is completed, whilst in the contact mode, the epidermis deforms under the pressure of the liquid, which allows all of the medicament to escape without achieving penetration.

Powered injectors generate higher pressure—typically 600 bars or more, which is sufficient to penetrate the epidermis even when the discharge orifice is placed firmly on the skin (the contact mode). However, even in the contact mode a variable quantity of liquid is lost on each injection because the epidermis initially deforms before puncturing, and allows some liquid to escape. A further reason that the contact mode injectors leak is that often the orifice fitted to the injector is an artificial jewel of the type used for bearings in chronometers (because they are inexpensive, accurate, and efficient), but the method of mounting the jewel is such that the face of the orifice is always a small distance from the skin, and the consequent broadening of the jet results in lower force per unit area, and poor penetration.

The basic aim of all these devices is to apply the medicament with sufficient force to pierce the epidermis, but it is the rate of increase in force which is important rather than the nominal pressure used, and few prior art injectors can achieve a sufficiently high rate of pressure rise to ensure reliable and repeatable injections.

Laboratory tests on both manual and powered injectors often give encouraging results, but in practical situations, such as the vaccination of animals, very variable amounts are injected—frequently over 50% of the vaccine may be wasted, because of hairs and dirt on the skin, and movement of the animal. The difficulty in achieving successful injections is exacerbated if the subject does not co-operate, as in the case of animals, young children or elderly patients. Premature operation of the injector is common, as is relative movement between the injector orifice and epidermis which can cause tearing of the epidermis during injection. The amount of contact pressure applied varies between operators, and the action of releasing the trigger mechanism frequently results in a jerk of the injector just as it operates, again causing poor injections and poor reproducibility.

Various methods have been proposed to overcome these problems, although in the case of the free jet types, little can be achieved. Powered injectors frequently employ a vacuum device to suck the epidermis firmly onto the discharge orifice (see WO 82/02835—Cohen, and EP-A-347190—Finger) and thereby improve the seal between the orifice and the epidermis, and prevent relative movement. Alternatively, a pressure sensitive sleeve on the injector (see U.S. Pat. No. 3,859,996—Mizzy) is placed on the subject, whereby operation of the injector is prevented until the correct contact pressure between the orifice and skin is achieved.

Powered injectors have available a variety of sensing and control devices to enhance their performance, which are denied to manually powered injectors. However, they are frequently more complex and not easily adapted for portable use. The fact that they develop higher pressures than manual injectors means that their power consumption is high; gas powered injectors require a heavy cylinder of compressed gas, and electrically powered injectors are often mains powered; battery powered injectors require a heavy battery pack, and the limited availability or inconvenience of the power sources has meant that the use of powered injectors has been mainly confined to mass vaccination programs. In the case of batteries and gas cylinders, it is usually difficult to judge the number of operations available from power stored. Furthermore, the sensing methods used to enable optimum operation are invariably secondary or indirect. For example, U.S. Pat. No. 3,859,996—(Mizzy) discloses a controlled leak method to ensure the injector orifice is correctly placed at the required pressure on the subject's skin. When the placement conditions are met, the controlled leak is sealed off by contact with the subject's skin, and the pressure within the injector control circuitry rises until a pressure sensitive pilot valve opens high pressure gas to the drive piston. However, the actual pressure of the orifice on the skin is not being measured; a hair of dirt of other irregularity on the skin or sealing face of the orifice will prevent or retard the pressure rise in the control circuit, and the operator will unconsciously press the injector harder onto the skin. Also the timing characteristics may vary because of the said ineffective sealing, hysteresis of the pressure switch, and variations in the supply pressure. In other words, the parameters being measured are the effectiveness of the seal of the controlled leak sensor on the skin and the pilot valve response, not the actual pressure of the orifice on the epidermis. Still other devices us a sliding sleeve in contact with the subject's skin, whereby displacement of the sleeve is used to initiate the injection, but this method measures the load on the sleeve, not on the orifice as required.

It may be seen therefore that whilst needle-less injection potentially is more efficient than hypodermic needle injections for certain applications, the technique is very dependent on the ability of the operator and the compliance of the subject. Those injectors that have features designed to reduce these problems tend to be more complex and costly, and less portable. Furthermore, the simpler injectors designed for use by the patient are invariably complicated to load, clean, adjust and operate, and have not been particularly well designed to be "user friendly". For example, self injection of insulin by the diabetic patient has been an area of intense development, because such patients often have to inject themselves four time daily, and needle-less injectors offer the possibility of less pain and tissue damage. Nevertheless, the aforesaid variability in performance has prevented the widespread adoption of the technique, and the recommended cleaning and sterilization procedures are extremely inconvenient.

WO 93/03779 describes a needle-less injector of the present inventor, which aims to overcome, or at least mitigate, the problems described above. In summary, it provides a needle-less injector which comprises a chamber for containing liquid to be injected, the chamber being provided with a liquid outlet; a dispensing member movable in a first direction to reduce the volume of the chamber to cause liquid contained therein to be expelled through the said liquid outlet; and an impacting member arranged to strike the said dispensing member to cause movement thereof in the said first direction; the injector comprising a front portion which carries means defining said liquid outlet, a rear portion having means defining a handle for the injector, means for urging the rear portion away from the front portion, and means for actuating the injector, or permitting actuation thereof, in response to the movement of the rear portion towards the front portion against the force of the means urging them away from one another.

The injector described in WO 93/03779 has been found to give excellent results. The design described in detail therein is, however, essentially one intended for dispensing a large number of doses, say 1500, and uses a built-in electric motor and battery to provide power. There remains a need, which has not been adequately met by the prior art, for a needle-less injector which is suitable for dispensing a single dose, or a small number of doses, and which is sufficiently inexpensive that it can be disposed of thereafter.

SUMMARY OF THE INVENTION

According to the present invention there is provided an actuator adapted, in conjunction with a cartridge, to form a needle-less injector, the cartridge being pre-filled with a liquid to be injected in a subject, and having a liquid outlet and a free piston in contact with the liquid, the actuator comprising an impact member urged by a spring and temporarily restrained by a latch means, the impact member being movable in a first direction under the force of the spring to first strike the free piston and then to continue to move the piston in the first direction to expel a dose of liquid through the liquid outlet, the spring providing a built-in energy store and being adapted to move from a higher energy state to a lower energy state, but not vice versa. The actuator may comprise trigger means to operate the said latch, and thus initiate the injection, only when a predetermined contact force is achieved between the liquid outlet of the said cartridge and the subject.

The term "liquid" as used herein includes, inter alia, solutions, suspensions, emulsions and colloids.

The cartridge is preferably a hollow cylindrical cartridge containing the medicament, having an outlet orifice which may be formed as part of the cartridge, or comprising a separate nozzle sealingly fitted to the outlet end of the cartridge. Preferably the cartridge is made of glass. The glass, or any alternative material of which the cartridge may be made, is preferably transparent, and may have markings to indicate the amount of medicament contained therein. The outlet orifice is that which is placed directly on the epidermis to cause the injection. The pre-filled cartridge may be supplied for insertion in the apparatus by the user, or supplied ready fixed onto the injector by the manufacturer.

In one aspect thereof, the invention provides a cartridge for use in conjunction with an actuator to form a needle-less injector, comprising a body which is of glass and a piston slidably mounted in the body and comprising a material which is substantially non-resilient when subjected to a slowly applied force but is highly resilient when subjected to a rapidly applied force. The preferred material for the cartridge body is polytetrafluoroethylene.

The cartridge may be a pre-filled cartridge as described heretofore, having an outlet end sealed by a frangible membrane. The cartridge can then be inserted into the apparatus and retained by a screw cap or similar device, interposed by a discharge nozzle with a piercing tube that punctures the frangible diaphragm so as to create an hydraulic connection with the medicament contained in the cartridge. Alternatively, the retaining cap may serve also as the nozzle, and have an integral piercing tube.

In an embodiment of the invention the spring may be a compression spring which acts against the impact member (hereinafter referred to as the "ram") which is restrained from movement by a manually adjustable nut and a latch. The nut may be adjusted away from its abutment, by an amount which represents the required stroke of the piston plus an acceleration distance between the ram face and the piston in the medicament cartridge, the ram being temporarily held by the latch. On disengaging the latch, the spring accelerates the ram in a forward direction so that it strikes the piston to give a high skin-piercing force within the medicament at the discharge orifice of the cartridge, and thereafter continues to move the piston to discharge the medicament until the nut comes to rest again on its abutment.

Thus it may be seen that if the aspects of the present invention as described above are combined, the device of the invention employs impact to create a high piercing pressure in the medicament, may dispense multiple doses from a pre-filled cartridge, has only one adjustment knob which sets the dose and the impact gap, and uses direct contact pressure sensing to initiate the injection and ensure repeatable performance. The injector may be configured as a single or multiple dose disposable item, supplied with the spring pre-loaded and the cartridge pre-filled, or with a facility for loading a fresh cartridge. The medicament may be a one-part or multi-part liquid or liquid and solid which may be mixed immediately prior to injection.

Injectors in which the power source is reloadable, for example the prior art devices which have a reloadable spring, must employ a certain factor of safety to ensure a reasonable working life. This is because as the spring is repeatedly stressed and unstressed it gradually loses its resilience. This loss is most pronounced if the spring is fully stressed at the start of each working cycle. It is therefore necessary to operate with the spring stressed to less than the maximum possible extent, say 60% of the maximum. By contrast, when using a spring which is non-reloadable during use of the device, as in the present invention, one can employ a spring which is loaded to the maximum possible extent. One can therefore have a spring which is smaller for a given amount of stored energy, or more powerful for a given size of a spring. Either way, one achieves a significant increase in the energy density of the device, i.e. the amount of energy stored per unit volume. Also by avoiding any need for a mechanism for reloading the spring, the size, weight and complexity of the device are reduced, and the problem of designing a reloading mechanism which is ergonomically correct is avoided.

One embodiment of the invention comprises a tubular body, one end of which terminates as a support plate with a co-axial hole therein, and the other end of which is configured to receive a cylindrical cartridge of liquid medicament. Passing through the hole in the support plate is a threaded rod, which is itself fully screwed into an internally threaded tube located within the tubular body. The threaded tube terminates in a curved face and further has an external shoulder on which a co-axially located compression spring abuts; this assembly constitutes a ram. The other end of the spring abuts at the outer face of the support plate and resiliently engages with one or more threads on the threaded rod. Before a cartridge is placed in the injector body, the spring is compressed by pressing on the curved face of the ram, and is held in the compressed condition by the latch.

The cartridge has a discharge nozzle at one end, and is sealed at the other end by a free sliding piston which is in contact with the medicament. The cartridge is located longitudinally within the tubular body against a shoulder in the tubular body, so that the piston contacts the curved face of the ram. The cartridge is retained in the tubular body by crimping or otherwise deforming the body around the orifice end of the cartridge, leaving a hole for the orifice.

A nut is screwed onto the threaded rod and reacts against the outside face of the support plate via a bridge over the latch. Initial rotation of the nut on the threaded rod in a first direction to a stop position further retracts the ram and creates a gap between the ram face and the piston. During the translation of the threaded rod, which is prevented from turning, the latch acts as a ratchet on the threads. The nut is then rotated in a second direction to a stop position where it locks onto the threaded rod, so that continued rotation now rotates the threaded rod also. The threaded rod unscrews from the internally threaded tubular member, so that there is now a gap between the abutment faces of the nut and support plate, which gap represents the impact distance plus the required stroke of the piston; the ram is prevented from forward movement of the latch. On disengagement of the latch, the spring accelerates the ram in a forward direction a distance set by the first rotation of the nut, so that it strikes the piston with considerable force, and then continues to push the piston for a distance determined by the gap set by the second rotation of the nut between the abutment faces of the nut and support plate, which distance is the sum of the impact gap and piston stroke. This cycle may be repeated until the spring is fully extended and all of the medicament is dispensed.

Operation of the latch is provided by a sliding sleeve assembled co-axially on the tubular body, and urged in a rearwards direction by a compression spring. In use, the injector orifice is placed on the subject's skin, and the injector is pushed firmly in the forward direction onto the skin by acting on the sliding sleeve. The sleeve moves forward against the force of the spring, and at a position representing the required contact force, a cam surface on the sleeve disengages the latch from the threaded rod, which accelerates under the action of the main spring to cause the injection, as described.

In another embodiment, the injector is configured as described, except that it allows a selected medicament cartridge to be installed by the user, and retained within the tubular body by a screwed or bayonet fitting cap. A variation of this embodiment is that the medicament cartridge is fitted with a frangible membrane seal instead of a discharge orifice, and the orifice is contained within the retaining cap, which has a piercing tube to puncture the membrane and make hydraulic connection with the medicament.

It is frequently desirable to inject a single dose of medicament and discard the injector after use, and another embodiment comprises a pre-filled cartridge of medicament having a free piston in contact with the medicament and an outlet orifice, retained in the injector casing, which casing supports a ram member urged by a spring but restrained by a latch. The latch may be a spring material and additionally bias a sliding trigger member, so that relative displacement of the trigger member to the injector casing against the bias disengages the latch and permits the ram to accelerate and strike the free piston, as described.

To enable the injection of two-part-drugs—for example a lyophilized (freeze dried) drug and a solvent—a further embodiment describes a method of storing and subsequently mixing the components prior to making an injection.

Embodiments are also described herein in which the gas spring rather than a compression spring, provided, for example, by compressed air with which a chamber in the injector is filled during manufacture.

DETAILED DESCRIPTION OF THE PREFERRED EMBODIMENTS

For convenience and to avoid confusion, like parts are given the same reference numerals throughout.

Figure 1:
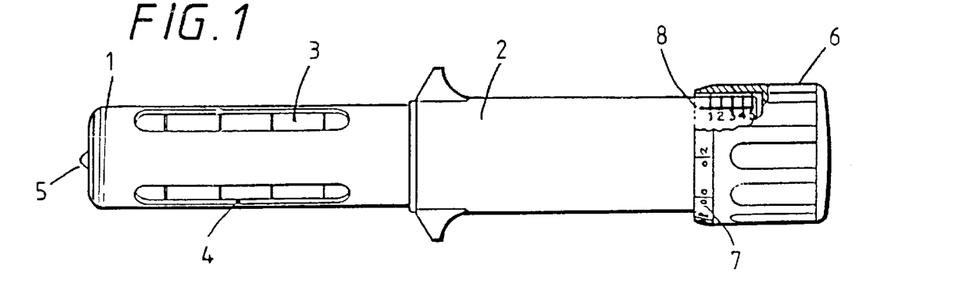
FIG. 1 is a general external view of the first embodiment of the injector, showing a plan elevation thereof.
Figure 1A:
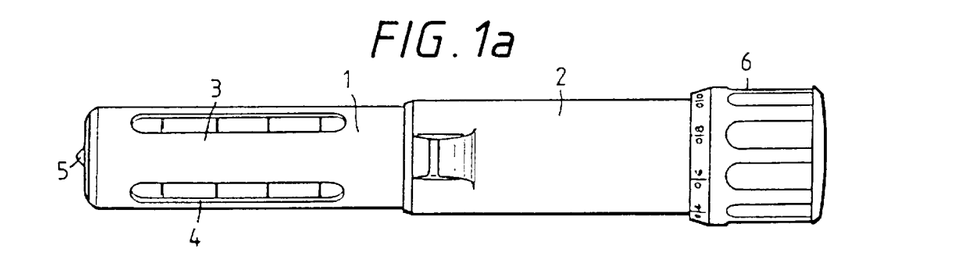
FIGS. 1a and 1b are side and end elevations respectively of the injector of FIG. 1.
Figure 1B:
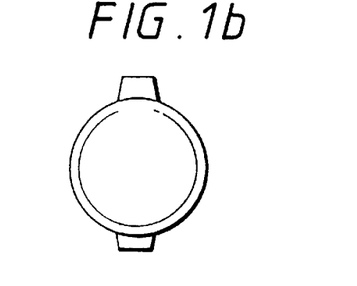

The injector shown in FIG. 1 comprises a tubular body 1, which retains a cartridge 3 pre-filled with medicament, and visible through one or more windows 4 in the body 1. The body 1 has an aperture in the end to permit a nozzle 5 to protrude. A finger nut 6 is used by the operator to control the dose volume, and has markings 7 thereon to indicate its position relative to a scale 8 on sliding sleeve 2, which is arranged co-axially on the body 1.

Figure 2:
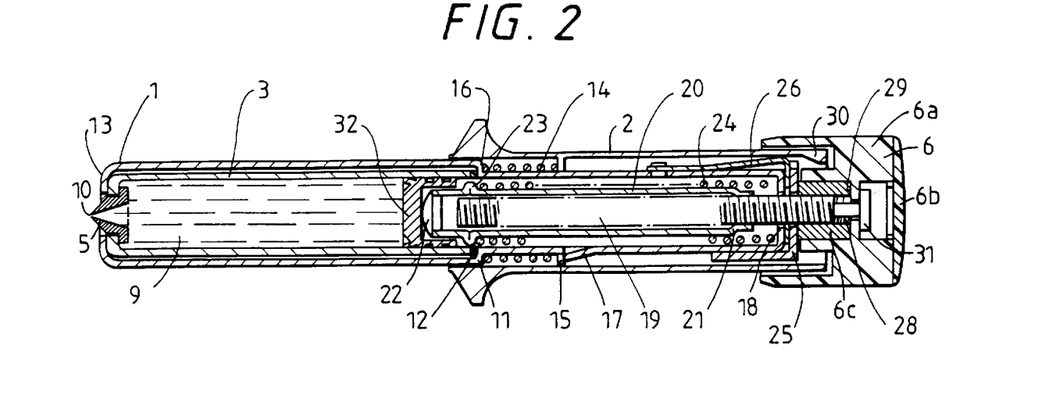
FIG. 2 is a longitudinal sectional view of the injector, fully loaded with medicament, as would be supplied in disposable form.

In FIG. 2, the cartridge 3 is shown filled with medicament, and fitted with a nozzle 5 having an orifice 10, and a free piston 32. The nozzle 5 may be a separate component as shown, sealingly fixed into the cartridge 3, or may be formed integrally with the cartridge 3. Preferably the cartridge 3 is made of a transparent material compatible with the medicament 9, to enable the contents to be viewed through the windows 4 in body 1. The cartridge 3 abuts a shoulder 11 formed on body 1, and is retained in this position by the crimped end 13 of body 1. The cartridge 3 is biassed toward the crimped end 13 by a resilient gasket or wave washer 12 interposed between shoulder 11 and an end face of the cartridge 3.

The sliding sleeve 2 is assembled co-axially on body 1 and is urged away from nozzle 5 by a spring 14 supported by a shoulder 16 on body 1 and acting on a shoulder 15. The extent of the rearward movement is limited by shoulder 15 resting on one or more stops 17. A cam 30 is formed inside the sleeve, so that when the sleeve is moved towards the nozzle 5, the cam strikes a latch 26 to initiate the injection.

Figure 2A:
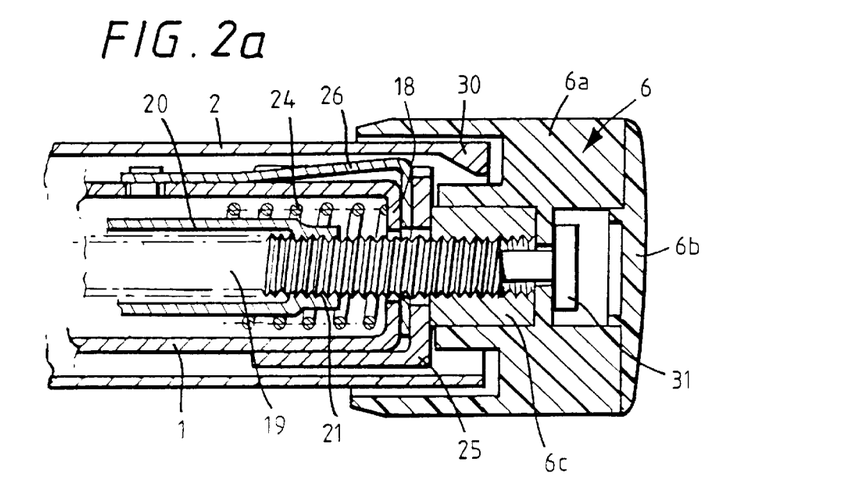
FIG. 2a shows the righthand portion of the actuator of FIG. 2, on a larger scale.

Support flange 18 is formed on the end of the body 1 and has a hole co-axially therein through which passes a threaded rod 19, which may be hollow to save weight. A tubular member 20 is located coaxially within the rear portion of the body 1 and has an internal thread 21 at one end into which the rod 19 is screwed. The other end of the tubular member 20 has a button having a convex face 22 pressed therein. Alternatively, the tubular member 20 may be formed to provide a convex face 22. A flange 23 is formed on the tubular member, and serves to support a spring 24, the other end of which abuts the inside face of support flange 18. In the position shown, the spring 24 is in full compression, and held thus by the nut 6 which is screwed onto threaded rod 19, and rests against the face of the bridge 25. In the illustrated embodiment the nut 6 consists of three components, held fast with one another, namely a body 6a, an end cap 6b and a threaded insert 6c. The insert 6c is the component which is screwed on to the rod 19, and is preferably made of metal, for example brass. The other components of the nut can be of plastics materials.

Figure 6:
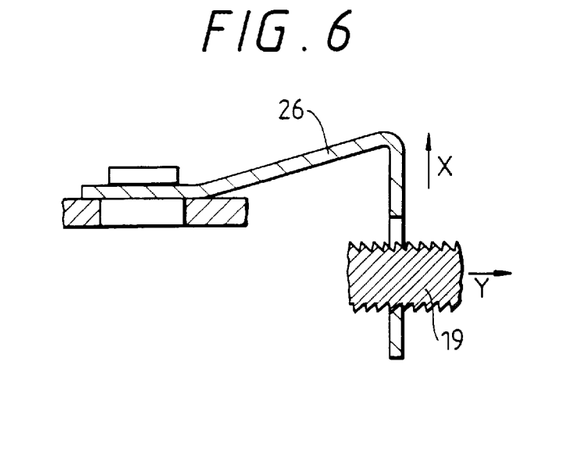
FIG. 6 is an enlarged longitudinal sectional view of the latch.
Figure 6A:
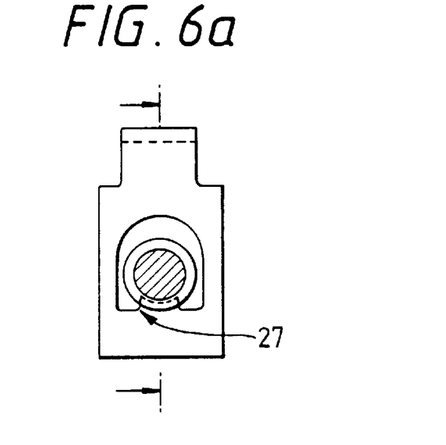
FIG. 6a is an enlarged end view of the latch.

Beneath the bridge and guided by same is a latch 26 which is attached to the body 1 and resiliently engaged with one or more threads on the screwed rod 19. The latch 26 is shown in more detail in FIG. 6, and is made from a spring material and has a projection 27 which has a partial thread form thereon, so that it engages fully with the thread formed on rod 19. The latch 26 is attached to body 1 and has a resilient bias in the direction of arrow X, thus maintaining its engagement with the thread on rod 19. Movement against the direction of arrow X disengages the latch from the thread. As will be described, the rod 19 will be translated without rotation in the direction of arrow Y when setting the impact gap, and the latch 26 will act as a ratchet pawl. The thread on rod 19 is preferably of a buttress form (each thread has one face which is perpendicular or substantially perpendicular, say at 5°, to the axis of the rod, and the other face is at a much shallower angle, say 45°), giving maximum strength as a latch member, and a light action as a ratchet member.

Referring again to FIG. 2, nut 6 is screwed part way onto threaded rod 19, so that there is a portion of free thread 28 remaining in the nut 6, defined by the end of rod 19 and stop face 29 in nut 6. A stop pin 31 has a head which bears against the stop face 29, and a shaft which is fixedly secured to the inside of rod 19, for example by adhesive. The stop pin 31 prevents the nut 6 being completely unscrewed from rod 19, since when the nut 6 is rotated anticlockwise, it will unscrew from the rod 19 only until the head of pin 31 contacts the face of the recess in the nut 6 in which it is located. The pin 31 also defines the maximum length of free thread in nut 6 when fully unscrewed.

Figure 3:
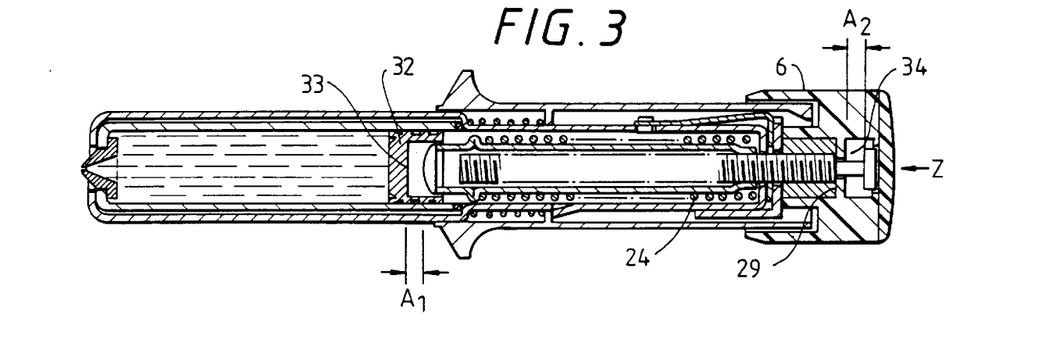
FIG. 3 is a view corresponding to FIG. 2, but showing the nut rotated in a first direction to create an impact gap between the ram face and medicament piston.

Referring to FIG. 3, the first stage in the operating cycle is to rotate the nut 6 on threaded rod 19 in a clockwise direction (assuming right-hand threads, and viewing in direction arrow Z). The rod 19 is prevented from turning, since the friction between the screw thread and the latch 26 is much higher than that between the nut 6 and the rod 19. This is mainly because the nut is unloaded, whereas the rod 19 has the full spring load engaging it with the latch 26. The rod 19 therefore moves into the nut 6 as far as the stop face 29. Alternative ways could be used to prevent the rod 19 from turning, for example using a ratchet or the like, or a manually operated detent pin. Since the threaded rod is attached to the tubular member 20, by the interengagement of the thread on rod 19 with the thread 21 on member 20, the latter is also moved rearwards (i.e. to the right as viewed in FIG. 2), increasing the compression on spring 24, and thus creates a gap $A_1$ between the convex face 22 of the tubular member 20 and the inner face 33 of piston 32. When the rod 19 is fully screwed into nut 6 the stop pin 31 projects a distance $A_2$ from face 34 which is equal to the gap $A_1$.

Figure 4:
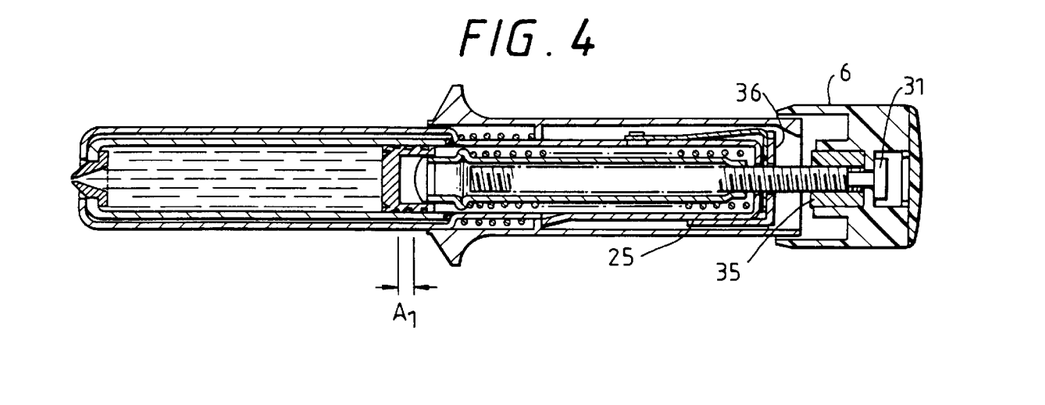
FIG. 4 shows the injector with the nut screwed out to set the stroke of the ram.

Referring to FIG. 4, nut 6 is now rotated anticlockwise until it contacts stop pin 31, which locks the nut 6 to the threaded rod 19. There is now a gap between face 35 on nut 6 and the abutment face 36, which gap is equal to gap $A_1$. Continued rotation of the nut now rotates the threaded rod also, because of the attachment of the shaft of the pin 31 to the side of the rod 19, and unscrews it in a rearward direction. The face 35 on nut 6 thus moves further away from its abutment face 36 on bridge 25. The increase in the gap is equivalent to the required stroke of the piston, and thus the total gap is the sum of the impact gap $A_1$ and the required stroke. The nut 6 has markings on the perimeter which are set to a scale on the sliding sleeve 2, in the manner of a micrometer. The zero stroke indication refers to the position of nut 6 when it first locks to the threaded rod 19, and immediately before the threaded rod is rotated to set the stroke.

Figure 5:
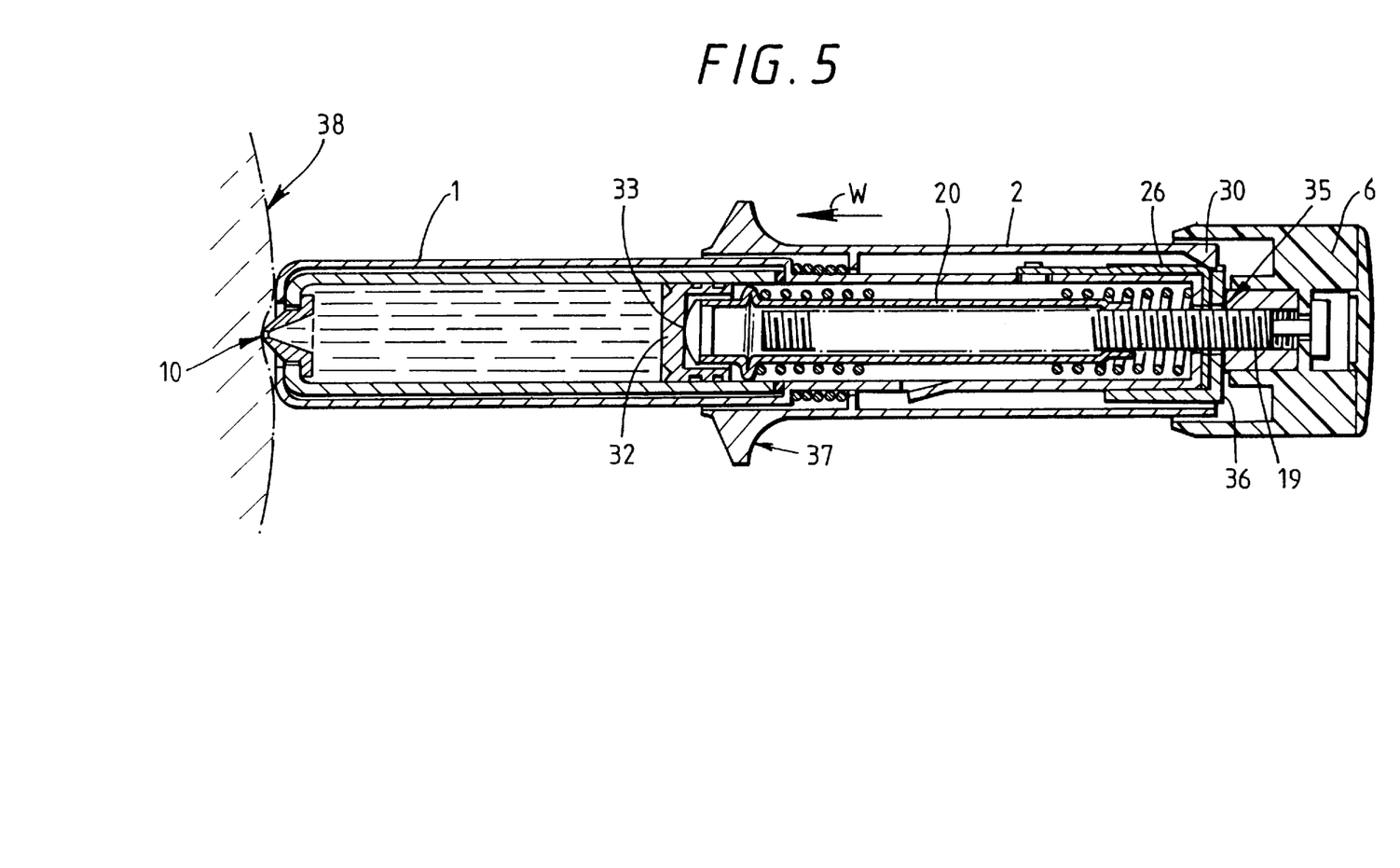
FIG. 5 corresponds to the previous views, but showing the components in a position immediately after injection, with the sliding sleeve disengaging the latch.

The injector is now ready to inject, and referring to FIG. 5, the injector is held in the hand by sliding sleeve 2, and the orifice 10 is placed on the epidermis 38 of the subject. Force is applied on the finger stops 37 in the direction of arrow W. The sliding sleeve 2 compresses spring 15 and moves towards the subject so that the force is transmitted through spring 14 to the body 1 and thus to the orifice 10, so as to effect a seal between the orifice 10 and epidermis 38. When the contact force has reached the predetermined level, the cam 30 on sliding sleeve 2 contacts latch 26 and disengages it from threaded rod 19. The spring 25 accelerates the tubular member 20 towards the piston through the distance $A_1$, and the convex face 22 strikes the face 33 of piston 32 with a considerable impact. The tubular member 20 thus acts as an impact member or ram. Thereafter the spring 24 continues to move the piston 32 forward until the face 35 on nut 6 meets the face 36 on bridge 25. The impact on the piston causes within the medicament a very rapid pressure rise—effectively a shock wave—which appears almost simultaneously at the injection orifice, and easily punctures the epidermis. The follow-through discharge of the medicament is at a pressure which is relatively low but sufficient to keep open the hole in the epidermis.

Spring 24 should be given sufficient pre-compression to ensure reliable injections throughout the full stroke of the ram. A 30% fall in force as the spring expands has been found to give reliable results. Alternatively, a series stack of Belleville spring washers in place of a conventional helical coil spring can give substantially constant force, although the mass and cost will be slightly higher.

The embodiment thus described provides an inexpensive, compact, convenient and easy-to-use disposable needle-less injector, capable of making sequential injections from a single cartridge of medicament. The power source is a spring which is pre-loaded by the manufacturer, and the medicament cartridge is also pre-filled and assembled into the injector. Thus the user merely rotates the single adjustment nut and presses the injector onto the epidermis, and the injection is triggered automatically. The size and mass of the injector will depend on the quantity of medicament contained therein, but typically, using a lightweight aluminium body and thin-walled construction where possible, a 5 ml injector would be about 135 mm long, 24 mm diameter (nut), with a mass of about 85 g including fluid.

Figure 7:
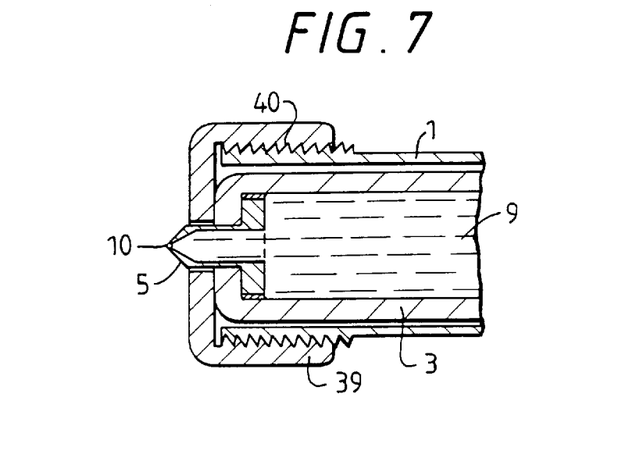
FIG. 7 shows part of the injector modified to allow a selected cartridge of medicament to be loaded.

It may be desirable to allow the user to select a particular medicament and actuator combination. For example, a veterinarian may have a large selection of doses and types of medicament, and may wish to combine one of these with an actuator that has characteristics suitable for the animal to be treated. FIG. 7 shows a modification to the injector to enable the user to install a fresh cartridge of medicament in the injector body 1. In this modification there is provided a thread 40 on body 1, and a screwed retaining cap 39 which clamps the cartridge 3 firmly against the resilient washer 12. Alternatively the cap 39 may have a bayonet connection with body 1.

Figure 8A:
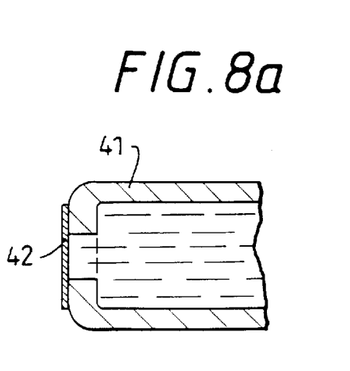
FIGS. 8a and 8b show respectively a cartridge having a frangible diaphragm seal and a nozzle cap fitted to same.
Figure 8B:
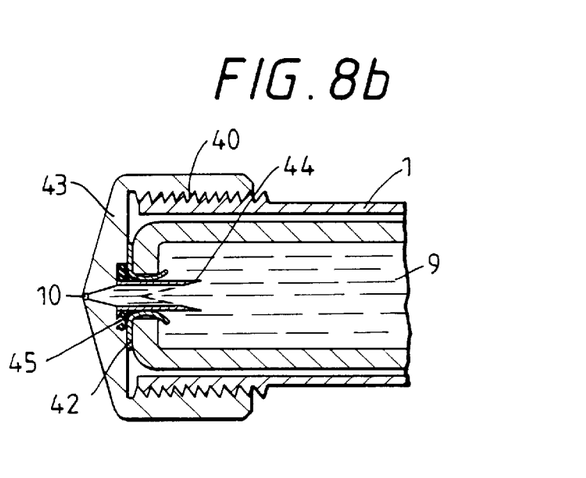

In the example of the second embodiment thus described the discharge orifice is shown as being part of the medicament cartridge. However, there may be occasions when a different nozzle may be required. For example the epidermis of piglets is vastly different to that of mature sows, and specially configured nozzles may be required. Or in the case of diabetic patients, the patient may find that a particular nozzle shape gives more comfortable injections. In a further modification, shown in FIGS. 8a and 8b, there is provided a cartridge 41 containing medicament 9, sealed with free piston 32 at one end, and having a frangible diaphragm seal 42 the other. Preferably the diaphragm material should be tearable and not break into small pieces when ruptured. Body 1 has a thread 40 on which may be screwed a nozzle 43, which also retains cartridge 41 within body 1. Nozzle 43 has a piercing tube 44 thereon, so that when the nozzle is first assembled onto the body 1, the piercing tube 44 ruptures the frangible diaphragm 42, making hydraulic connection with the medicament 9. Sealing of the nozzle 43 to the cartridge 41 is effected by a seal 45. Alternatively there may be provided a separate nozzle and retaining cap (not shown) which will serve an equivalent function. The cartridge with a frangible seal will be less expensive that the cartridge having an integral nozzle, and this may be important when large numbers of cartridges are used, as would be the case with insulin for example.

Figure 9A:
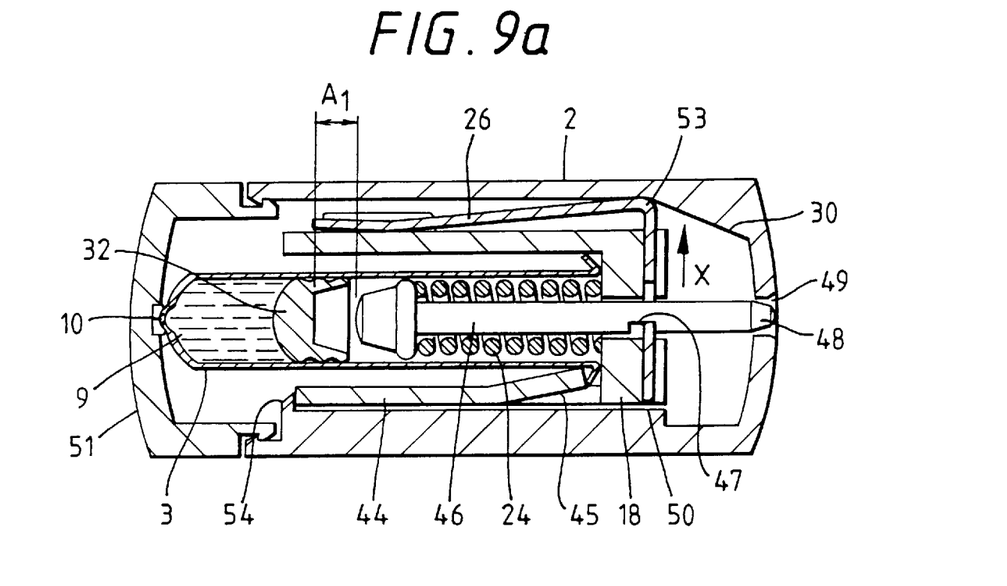
FIGS. 9a and 9b depict a single dose disposable injector, ready to use and injecting medicament into the tissues of a subject.
Figure 9B:
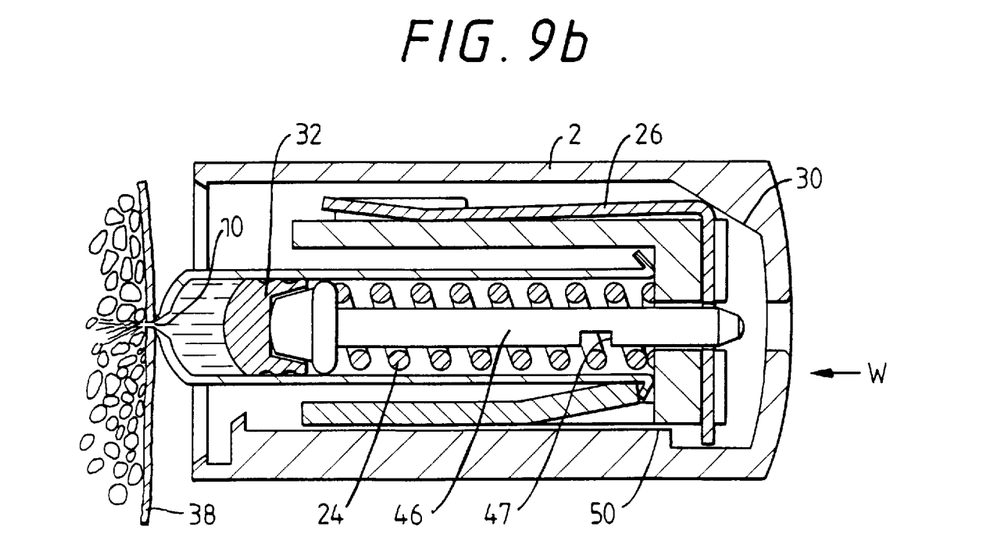

The embodiment shown in FIGS. 9a and 9b is a single use disposable injector. Referring to FIG. 9a, cartridge 3 containing medicament 9 and free piston 32 is firmly located in the injector casing 44 and retained by one or more resilient lugs 45, so that there is no longitudinal free play. A ram 46 is located concentrically with the cartridge and such that there is an impact gap $A_1$ between the adjacent faces of the piston 32 and ram 46. Ram 46 is urged towards piston 32 by spring 24, but is prevented from moving by latch 26 supported on flange 18 and engaged with notch 47 in the stem of the ram 46. Latch 26 is made from a resilient material, and is configured to apply a bias in the direction of arrow X. A sliding sleeve 2 is located over the casing 44, with cam surface 30 just touching the bend 53 on latch 26, and retained on casing 44 by lug 54. Thus the latch 26 acts also as a spring to bias the sleeve 2 in direction of arrow X relative to the casing 44. The medicament 9 and orifice 10 are protected by a cap 51 snap fitted to the sliding sleeve 2 as shown, or attached to the cartridge 3. Distal end 48 of ram 46 is located within aperture 49 in sliding sleeve 2, giving visual and tactile indication that the injector is loaded and ready for use.

Referring now to FIG. 9b, to make an injection, cap 51 is removed and the orifice 10 is placed on the subject's skin 38, with the axis of the injector approximately normal to the skin. Sufficient force is applied on sliding sleeve 2 in the direction of arrow W to overcome the biassing force of the latch 26 on cam surface 30. The sleeve 2 moves in the direction of arrow W and the cam surface 30 thus disengages the latch 26 from the notch 47 in ram 46 which is then rapidly accelerated by spring 24 to strike piston 32, and the injection is accomplished as previously described. The point at which the latch 26 disengages from the ram 46 is directly related to the reaction force on the subject's skin, and by suitable selection of components, accurate and repeatable placement conditions may be met, ensuring predictable triggering of the injection. A safety bar 50 on sliding sleeve 2 prevents accidental disengagement of the latch 26 (by dropping, for example), and this safety feature may be augmented by a manually operated detent (not shown) that prevents movement of the sliding sleeve 2 until operated. In an alternative arrangement (not shown) the latch 26 may be biassed in the opposite direction to that described, so that it tries to disengage itself from the notch 47 but is prevented from doing so by by a bar on sliding sleeve 2. Movement of the sliding sleeve 2 and bar permits the latch 26 to disengage itself from the notch 47, thus initiating the injection: in this example a separate spring means may be required to bias the sliding sleeve 2 against the direction of arrow W.

Figure 10A:
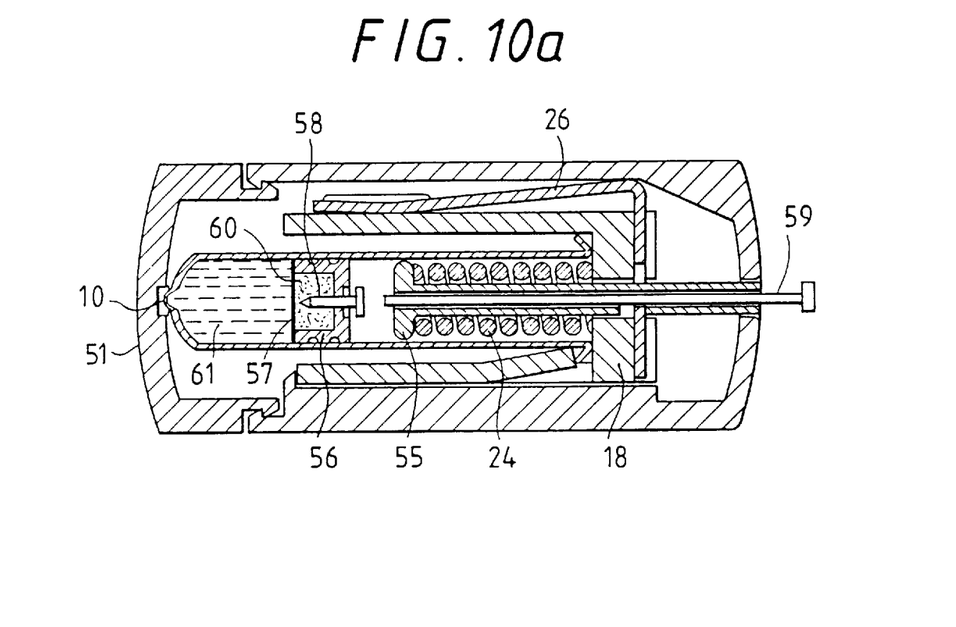
FIGS. 10a and 10b show a single dose disposable injector in which the free piston is adapted to store a component of a two-part medicament, and having means to connect the components and mix them before injection.
Figure 10B:
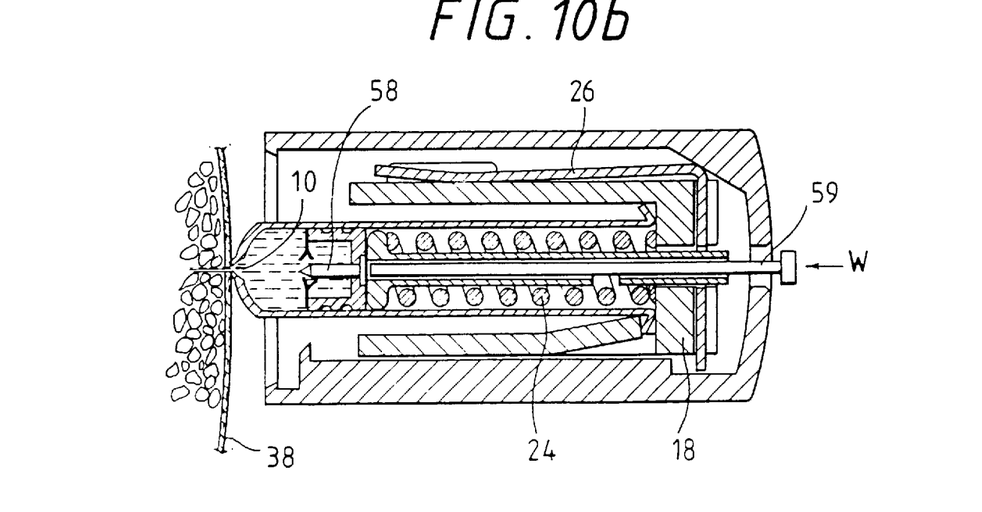

The embodiment shown in FIGS. 10a and 10b is similar to that shown in FIGS. 9a and 9b and described above, but modified to permit the storage of a lyophilized drug and solvent, or other two-part formulations. FIG. 10a shows a single dose injector, loaded and ready for use. Free piston 56 is hollow and stores one component 60 of the medicament—for example a lyophilized drug—which is retained in piston 56 by frangible membrane 57 which also separates the drug 60 from its solvent 61 stored in cartridge 3. A membrane cutter 58, which has one or more cutting edge, is sealingly and slidingly located in piston 56, so that its cutting edge is a small distance from the frangible membrane 57. Ram 55 is hollow, and located within its bore is a cutter operating rod 59. Referring also to FIG. 10b, the rod 59 is pushed in the direction of arrow W so that it acts on membrane cutter 58. The membrane cutter 58 cuts membrane 57, thus allowing the solvent 61 to mix with and dissolve the drug 60. The injector may be agitated to accelerate the mixing process. Throughout the membrane cutting and mixing period, protective cap 51 seals orifice 10 to prevent loss of fluid. After sufficient time has elapsed to ensure thorough dissolution of the drug, cap 51 is removed, orifice 10 is placed on the subject's skin, and the injection is accomplished as previously described.

Except during the injection, the main reaction forces of the spring 24 and the latch 26 are taken on the support flange 18. During the injection, although the shock forces are high, they are of very short duration, and therefore the body components may be of very lightweight construction. Thus, although the use of thin metal tube is described in the embodiments, plastics may be used for most structural parts because they would not be subject to sustained forces which could lead to creep and distortion.

Whilst the shape of the nozzle may be such to achieve optimum sealing efficiency and comfort, the geometry of the orifice within the nozzle should have a length to diameter ratio of preferably not more than 2:1, preferably in the order of 1:2, and the exit of the orifice should be placed directly onto the epidermis. It is sometimes necessary to use multiple orifice nozzles, particularly when dispensing large volumes, and each orifice in the nozzle should ideally have a maximum L:D ratio of 2:1, preferably 1:2.

In the embodiments described, the force to move the ram is provided by a spring, as described, a compression spring) which is initially in its high energy state (i.e. compressed in the case of a compression spring). The ram member is moved by permitting the spring to move to a lower energy state (i.e. uncompressed, or less compressed, in the case of a compression spring). In contrast, the embodiment described below with reference to FIGS. 11, 11a and 11b uses gas under pressure to provide the driving force for the ram.

Figure 11:
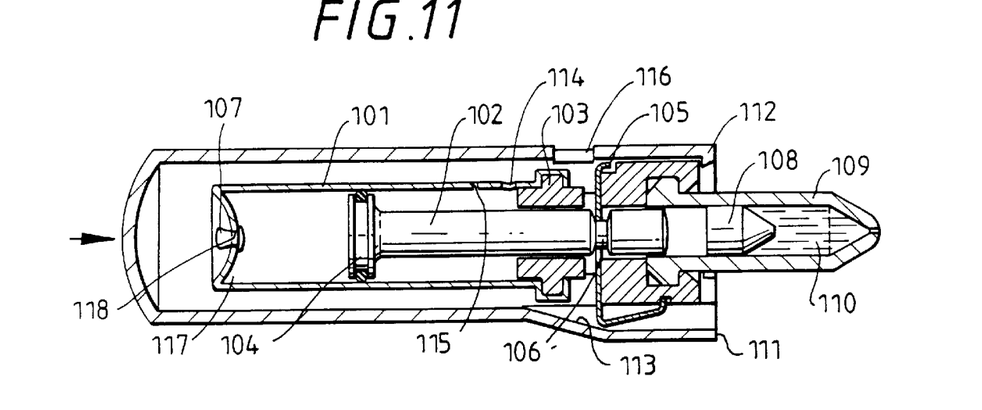
FIGS. 11, 11a and 11b show a further embodiment of the invention in, respectively, longitudinally section view before use, cross section view, and longitudinal sectional view after firing.
Figure 11A:
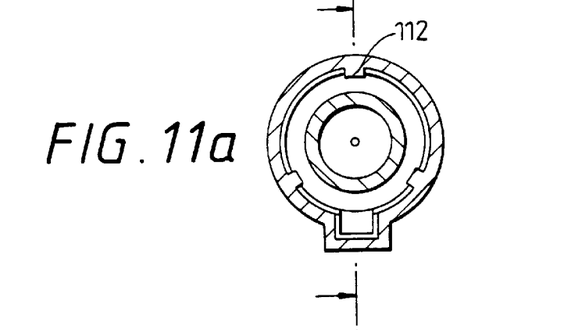

The illustrated embodiment comprises a gas cylinder 101 containing a ram 102 having piston end 104 sealingly and slidingly fitted into cylinder 101. The ram 102 is guided in a bush 103, and temporarily retained from longitudinal movement by a spring latch 105 engaged in a detent groove 106. The bush 103 is crimped or otherwise retained in cylinder 101 so as to withstand forces created during storage and operation of the injection which would otherwise cause the cylinder and bush to separate.

Gas, such as air, at high pressure, is introduced through a filling hole 118 into a chamber 117 and sealed by an elastomeric bung 107. Thus, piston 104 and ram 102 are urged in a first direction, but retained from movement by the latch 105 engaged in the detent 106. It is to be noted that the gas in chamber 117 applies pressure directly to the piston and thus exerts a force on the piston at all times. A cartridge 109 containing drug 110 and a device piston 108 is firmly fitted into bush 103. An outer case 111 is slidingly fitted over the assembly of cylinder 101 and bush 103, and restrained from coming off the assembly by one or more retaining lugs 112. The injector is now ready for use.

To operate the injector, the drug cartridge is placed on the subject's skin, and the outer case is pressed in the direction of the skin. A cam 113 integral with case 111 pushes on latch 105 to disengage the latch from the detent groove 106 on the ram 102. The ram 102 is thus able to accelerate rapidly under the action of pressurised gas in chamber 117 on drive piston 104, and strikes drivably piston 108 to cause the injection.

To prevent inadvertent operation, the latch 105 cannot disengage from the detent 106 until a slot 116 in the wall of the case 111 is moved in the said first direction when initiating the injection. A further safety feature (not shown) is a removable plug which fits into hole 116 and prevents operation of latch 105 until removed.

Figure 11B:
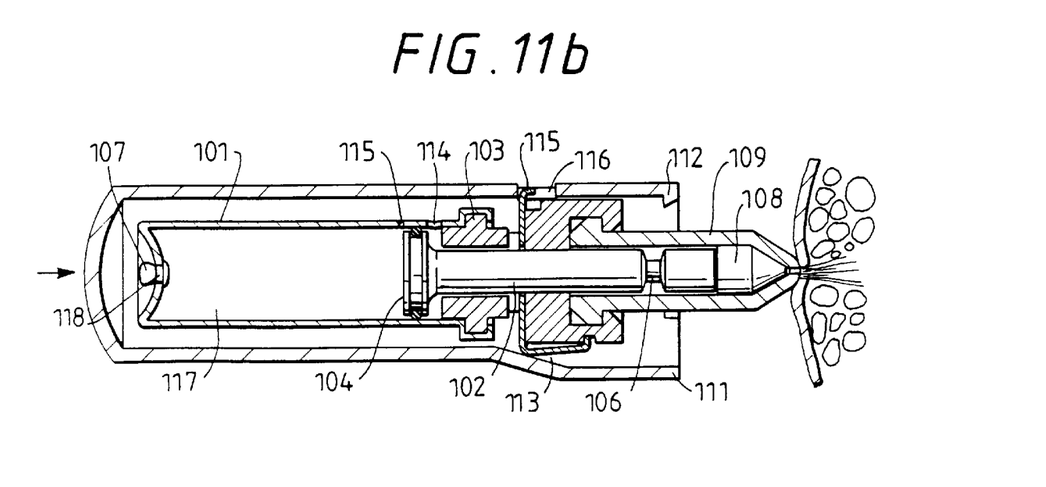

When piston 104 moves in the first direction the air trapped in the low pressure part of the cylinder 101 is allowed to escape through a vent 114. When the piston 104 comes to rest, residual pressurised gas in chamber 117 is allowed to bleed away through a safety bleed hole 115, which is of small area so as not to adversely affect the final part of the stroke of the piston 104 as it uncovers the hole 115.

As mentioned earlier, the cartridges used in the present invention are preferably made of glass. In a preferred embodiment thereof, the forward end of each cartridge has a circular hole of preferably from 0.15 to 0.3 mm diameter formed therein as the outlet orifice. The free piston in the cartridge is of a suitably inert material, and polytetrafluoroethylene (PTFE) is preferred as the material for the whole or part thereof. PTFE has the advantage that its coefficients of static and dynamic friction are similar to one another and extremely low (about 0.01). It also has the property that it is substantially non-resilient when subjected to a slowly applied force but is highly resilient when subjected to a rapidly applied force. This makes it particularly suitable for use in the context of the present invention, where a rapidly applied force is exerted on the piston at the time of impact. Other materials which can be used instead of PTFE, or in combination therewith, include tetrafluoroethylene-hexafluoropropylene copolymer, tetrafluoroethylene-ethylene copolymer, polychlorotrifluoroethylene, poly (vinylidene fluoride), tetrafluoroethylene-perfluoro(propyl vinyl ether) copolymer, and hexafluoroisobutylene-vinylidene fluoride copolymer. Yet another material which can be used is acetal, though this is believed not to have the resilient/non-resilient property which characterises PTFE. The initial diameter of the free piston, at least when made of PTFE, can be greater than the internal diameter of the cartridge by up to about 0.25 mm. When forced into the cartridge, the creep of the PTFE is sufficient to allow this, and the resulting seal between the piston and wall of the cartridge is excellent.

What is claimed is:

1. An actuator for use in conjunction with a cartridge to form a needle-less injector, the cartridge being prefilled with a liquid to be injected in a subject, the cartridge having a liquid outlet and a free piston inward of the liquid outlet in contact with the liquid, said actuator comprising:

(a) a housing having a forward portion adapted to be connected with the cartridge;

(b) impact member mounted within said housing inward of the forward portion so as to be movable from a first position toward the forward portion to strike the free piston when a cartridge is connected and to continue to move the free piston toward the liquid outlet whereby a dose of the liquid is expelled through the liquid outlet in the cartridge;

(c) a chamber within said housing prefilled with pressurized gas and connected with said impact member such that said pressurized gas is constantly in communication with and constantly exerts a force on said impact member to normally urge said impact member toward the liquid outlet; and (d) a latch within said housing which engages said impact member to prevent movement of the impact member toward the forward portion in response to said force exerted by said pressurized gas, and being mounted to be movable out of engagement with said impact member to a firing position, in which said latch permits such movement.

2. The actuator as claimed in claim 1, further comprising a gas outlet defined in said chamber for allowing residual gas to escape from said chamber after said dose of liquid has been expelled.

3. The actuator as claimed in claim 2, further comprising a cam engageable with said camming surface to move said latch to said firing position.

4. An actuator as claimed in claim 1, wherein said pressurized gas is air.

5. An actuator as claimed in claim 1, further comprising trigger means for operating said latch to thus initiate the injection in response to a predetermined contact force between the liquid outlet of the cartridge and the subject.

6. An actuator as claimed in claim 5, wherein said actuator has a user-holdable portion and means for mounting the cartridge so that the user-holdable portion is movable relative to the cartridge by the liquid outlet of the cartridge being urged into contact with the subject, and said latch comprises a latch member which is movable to said firing position by the relative movement between the user-holdable portion and the cartridge.

7. An actuator as claimed in claim 6, wherein said latch member is resilient.

8. An actuator as claimed in claim 1, wherein the energy stored by said pressurized gas is sufficient to expel a single dose of the liquid.

9. An actuator as claimed in claim 1, wherein the energy stored by said pressurized gas is sufficient to expel a plurality of successive doses of the liquid.

10. An actuator as claimed in claim 1, in combination with a connected cartridge that includes a separately held plurality of components which are to be mixed with one another prior to injection and a mixing member for mixing the plurality of components with one another, said impact member further comprising a mixing means being movable toward the liquid outlet for striking the mixing member, whereby the plurality of components are mixed with one another.

11. The actuator as claimed in claim 2, wherein said chamber is sealed.

12. An actuator as claimed in claim 1, wherein the movement of said impact member expels a fixed dose.

13. An actuator as claimed in claim 1, wherein the distance of travel of said impact member after striking the free piston determines the dose of the liquid expelled through the liquid outlet in the cartridge.

14. An actuator as claimed in claim 1 in combination with a cartridge, comprising means for retaining said cartridge for engagement with said actuator, said retaining means being constructed to permit the fixed mounting of said cartridge.

15. An actuator as claimed in claim 1, having means for removably receiving the said cartridge.

16. An actuator as claimed in claim 15 in combination with a cartridge, comprising means for retaining said cartridge for engagement with said actuator, said retaining means being constructed to permit removal of said cartridge.

17. The combination as claimed in claim 16, wherein said cartridge has a body comprising glass.

18. The combination as claimed in claim 17, wherein said glass is transparent.

19. The combination as claimed in claim 16, wherein said free piston of said cartridge comprises a plastics material.

20. The combination as claimed in claim 19, wherein said plastic material is a polymer or copolymer comprising a fluorinated hydrocarbon.

21. The combination as claimed in claim 19, wherein said plastic material is a polytetrafluoroethylene.

22. The combination as claimed in claim 19, wherein said plastic material is selected from the group consisting of tetrafluoroethylene-hexafluoropropylene copolymer, tetrafluoroethylene-ethylene copolymer, polychlorotrifluoroethylene, poly (vinylidene fluoride), tetrafluoroethylene-perfluoro(propyl vinyl ether) copolymer, and hexafluoroisobutylene-vinylidene fluoride copolymer.

23. An actuator in combination with a cartridge to form a needle-less injector, comprising:

(a) said cartridge being prefilled with a liquid to be injected in a subject, said cartridge comprising,
  (i) a liquid outlet and a free piston inward of the liquid outlet in contact with the liquid;
  (ii) a separately held plurality of components which are to be mixed with one another prior to injection; and
  (iii) a mixing member for mixing the plurality of components with one another, wherein the plurality of compartments are separated by at least one partition and said cartridge further has a penetrating member so mounted therein as to be movable to a mixing position in which it penetrates the partition; and (b) said actuator comprising:
  (i) a housing adapted to be connected with the cartridge;
  (ii) impact member mounted within said housing inward of the free piston so as to be movable from a first position toward the liquid outlet to strike the free piston and to continue to move the free piston toward the liquid outlet whereby a dose of the liquid is expelled through the liquid outlet in the cartridge, said impact member further comprising a mixing means being movable toward the liquid outlet for striking the mixing member, said mixing means in striking said mixing member being further operable to move the penetrating member to the mixing position whereby the plurality of components are mixed with one another;
  (iii) a sealed chamber within said housing prefilled with pressurized gas and connected with said impact member such that said pressurized gas constantly exerts a force on said impact member when said impact member is in said first position to normally urge said impact member toward the liquid outlet; and
  (iv) a latch within said housing for engaging said impact member to prevent movement of the impact member toward the liquid outlet in response to said force exerted by said pressurized gas, and being movable to a firing position for permitting such movement.

24. A method of injecting a dose of liquid in a subject using
- an injector including a cartridge prefilled with the liquid and having a liquid outlet and a free piston in contact with the liquid,
- an impact member movable from a first position behind the free piston to first strike said free piston and then to continue to move the piston toward said liquid outlet to expel a dose of liquid through said liquid outlet;
- a chamber prefilled with pressurized gas which constantly contacts and exerts a force on said impact member in said first position to urge said impact member towards said piston
- a latch movable from a restraining position, in which said latch engages and prevents movement of the said impact member in response to the force exerted by the gas, to a firing position, in which said latch does not engage said impact member and permits such movement;
- (ii) causing said latch to move from said restraining position said method comprising the steps of to said firing position, whereby said impact member moves toward the liquid outlet, strikes said free piston, and continues to move said piston toward the liquid outlet to expel a single dose of said liquid.

25. The method of injecting a dose of liquid in a subject as claimed in claim 24, further comprising the step of disposing of said injector after the single dose has been expelled.

* * * * *

UNITED STATES PATENT AND TRADEMARK OFFICE
CERTIFICATE OF CORRECTION

PATENT NO.   : 5,891,086
DATED        : April 6, 1999
INVENTOR(S)  : Weston

It is certified that error appears in the above-identified patent and that said Letters Patent is hereby corrected as shown below:

Column 16, claim 24,
Lines 5 and 6, please delete "(ii) causing said latch to move from said restraining position said method comprising the steps of to said" and insert therefor -- said method comprising the step of causing said latch to move from said restraining position to said --.

Signed and Sealed this

Fourth Day of December, 2001

*Attest:*

*Attesting Officer*

NICHOLAS P. GODICI
*Acting Director of the United States Patent and Trademark Office*